United States Patent
Conlin et al.

(10) Patent No.: US 11,056,229 B2
(45) Date of Patent: Jul. 6, 2021

(54) SYSTEMS, METHODS, AND MEDIA FOR LABORATORY BENEFIT SERVICES

(71) Applicant: Laboratory Corporation of America Holdings, Burlington, NC (US)

(72) Inventors: Paul Conlin, Burlington, NC (US); Roberto Verrengia, Burlington, NC (US); Louis Engel, Burlington, NC (US)

(73) Assignee: Beacon Laboratory Benefit Solutions, Inc., Montvale, NJ (US)

( * ) Notice: Subject to any disclaimer, the term of this patent is extended or adjusted under 35 U.S.C. 154(b) by 0 days.

(21) Appl. No.: 13/800,450

(22) Filed: Mar. 13, 2013

(65) Prior Publication Data

US 2013/0197943 A1    Aug. 1, 2013

Related U.S. Application Data

(63) Continuation-in-part of application No. 13/723,271, filed on Dec. 21, 2012, now abandoned, and a
(Continued)

(51) Int. Cl.
*G16H 40/20* (2018.01)
*G16H 50/20* (2018.01)
(Continued)

(52) U.S. Cl.
CPC ......... *G16H 40/20* (2018.01); *G06F 16/2471* (2019.01); *G16H 10/40* (2018.01);
(Continued)

(58) Field of Classification Search
None
See application file for complete search history.

(56) References Cited

U.S. PATENT DOCUMENTS

| 5,164,575 | A | 11/1992 | Neeley et al. |
| 6,372,182 | B1 * | 4/2002 | Mauro ............... A61B 10/0045 422/417 |

(Continued)

OTHER PUBLICATIONS

Patent Cooperation Treaty, International Search Report and Written Opinion, International Application No. PCT/US12/71197, dated Mar. 5, 2013.
(Continued)

*Primary Examiner* — Amresh Singh
*Assistant Examiner* — Edward Jacobs
(74) *Attorney, Agent, or Firm* — Kilpatrick Townsend & Stockton LLP

(57) ABSTRACT

Systems, methods, and media for laboratory benefit services are disclosed. Embodiments of the present invention provide systems, methods, and media that enhance the quality of health care related services to a patient, thereby enhancing patient care.
In an embodiment, the present invention provides systems, methods and media that present a health care provider with information to support a decision, for example, a decision relating to a test, or tests, for a patient. In addition, or in additional embodiment, the present invention provides systems, methods and media that present information relating to a patient's health plan to advantageously facilitate a health care provider's knowledge and use of a patient's health plan information. Further, or in an additional, or further, embodiment, the present invention provides systems, methods and media that present information relating to a laboratory to advantageously facilitate a health care provider's knowledge and use of laboratory information, including laboratory expertise.

23 Claims, 2 Drawing Sheets

Related U.S. Application Data continuation of application No. 13/723,384, filed on Dec. 21, 2012, now Pat. No. 10,664,486.

(60) Provisional application No. 61/584,936, filed on Jan. 10, 2012, provisional application No. 61/578,529, filed on Dec. 21, 2011.

(51) Int. Cl.
*G06F 16/2458* (2019.01)
*G16H 10/40* (2018.01)
*G16H 70/60* (2018.01)

(52) U.S. Cl.
CPC .............. *G16H 50/20* (2018.01); *G16H 70/60* (2018.01); *Y02A 90/10* (2018.01)

(56) References Cited

U.S. PATENT DOCUMENTS

| | | | |
|---|---|---|---|
| 2002/0010625 A1* | 1/2002 | Smith | G06Q 30/02 705/14.52 |
| 2002/0147596 A1 | 10/2002 | Vanderboom et al. | |
| 2002/0161606 A1 | 10/2002 | Bennett et al. | |
| 2007/0016102 A1 | 1/2007 | Askin | |
| 2007/0294103 A1 | 12/2007 | Ahmed et al. | |
| 2008/0050278 A1* | 2/2008 | Farina | G01N 35/00 422/64 |
| 2008/0195421 A1 | 8/2008 | Ludwig et al. | |
| 2009/0198520 A1 | 8/2009 | Piovanetti-Perez | |
| 2010/0036677 A1 | 2/2010 | Daub, Jr. et al. | |
| 2010/0169263 A1* | 7/2010 | Korpman | G16H 50/20 706/50 |
| 2011/0029322 A1 | 2/2011 | Hindo et al. | |
| 2011/0153357 A1 | 6/2011 | Zubiller et al. | |
| 2011/0161106 A1 | 6/2011 | Chapman et al. | |
| 2011/0251960 A1 | 10/2011 | Holla et al. | |
| 2011/0265195 A1* | 10/2011 | Chang | A61K 39/245 800/13 |
| 2012/0016685 A1 | 1/2012 | Ryan et al. | |

OTHER PUBLICATIONS

Patent Cooperation Treaty, International Search Report and Written Opinion, International Application No. PCT/US12/71167, dated Mar. 5, 2013.
Patent Cooperation Treaty, International Preliminary Report on Patentability, International Application No. PCT/US12/071167 dated May 14, 2015.
U.S. Appl. No. 13/723,384, Final Office Action dated Nov. 23, 2015, 20 pages.
U.S. Appl. No. 13/723,384, Non-Final Office Action dated Oct. 6, 2014, 19 pages.
U.S. Appl. No. 13/723,384, Non-Final Office Action dated Oct. 11, 2016, 23 pages.
Canadian Patent Office Application 2,858,355, Office Action dated Aug. 6, 2015, 3 pages.
Canadian Patent Office Application 2,858,355, Office Action dated Oct. 18, 2016, 4 pages.
Canadian Patent Office Application 2,859,843, Office Action dated Nov. 1, 2016, 5 pages.
Canadian Patent Office Application 2,859,843, Office Action dated Dec. 10, 2015, 9 pages.
Austin Community College; "Exercise 2: Venipuncture using vacuum collection system" ; Sep. 5, 2007; pp. 13-40.
U.S. Appl. No. 13/723,384, Final Office Action dated Jun. 16, 2017.
U.S. Appl. No. 13/723,384, "Non-Final Office Action", dated Jan. 4, 2018, 22 pages.
CA 2,858,355, "Office Action", dated Aug. 28, 2017, 4 pages.
U.S. Appl. No. 13/723,271 , "Non-Final Office Action", dated May 7, 2014, 33 pages.
U.S. Appl. No. 13/723,384 , "Final Office Action", dated Jun. 28, 2018, 28 pages.
U.S. Appl. No. 13/723,384 , "Non-Final Office Action", dated May 31, 2019, 4 pages.
U.S. Appl. No. 13/723,384 , "Notice of Allowance", dated Aug. 28, 2019, 7 pages.
CA2,858,355 , "Notice of Allowance", dated May 14, 2019, 1 page.
CA2,858,355 , "Office Action", dated Jun. 26, 2018, 3 pages.
PCT/US2012/071197 , "International Preliminary Report on Patentability", May 14, 2015, 8 pages.

* cited by examiner

SYSTEMS, METHODS, AND MEDIA FOR LABORATORY BENEFIT SERVICES

CROSS-REFERENCE TO RELATED APPLICATION

This application claims priority under 35 U.S.C. 119 to U.S. Provisional Patent Application No. 61/584,936, filed Jan. 10, 2012, entitled "Systems, Methods, and Media for Laboratory Testing Services," and to U.S. Provisional Patent Application No. 61/578,529, filed Dec. 21, 2011, entitled "Systems, Methods, and Media for Laboratory Testing Services;" and claims priority under 35 U.S.C. 120 to U.S. Utility patent application Ser. No. 13/723,271, filed Dec. 21, 2012 entitled Systems, Methods and Media for Laboratory Testing Services; and to U.S. Utility patent application Ser. No. 13/723,384, filed Dec. 21, 2012 entitled Systems, Methods and Media for Laboratory Testing Services, the entirety of each of the priority applications being hereby incorporated by reference.

FIELD OF THE INVENTION

This disclosure relates generally to health care delivery and more particularly to systems, methods and media that provide users of a health care system information, such as information relating to laboratory tests and health plans. This disclosure also relates to systems, methods and media that provide decision support to health care providers. This disclosure further relates to systems, methods and media that facilitate interaction between and among health care providers, health insurers/insurance plans, laboratories and/or patients. In addition, or in combination, this disclosure generally relates to laboratory benefit services.

BACKGROUND

Health care providers desire to provide the best care to their patients and, in doing so, often need to select laboratory tests. It is advantageous for health care providers to select the optimal test, or tests, for their patient, to know the proper timing of selected tests, and to be able to differentiate the labs that have the expertise to perform the selected tests. It is also advantageous for health care providers and patients to be able to understand insurance coverage relating to laboratory tests.

Health plans and self-funded employer groups are seeking better and easier ways to improve patient care and physician support while managing laboratory utilization and costs. As the number of laboratories, laboratory tests, health plans, and medical codes have increased, the complexity of managing the ordering, delivery, and fulfillment of laboratory tests has also increased. Systems and methods that reduce the complexity of ordering laboratory tests, and support health care providers in the ordering of the laboratory tests would be advantageous. Systems and methods that increase the efficiency of the delivery of health care services to a patient, would be also advantageous. Furthermore, systems and methods that increase the efficiency of the delivery of health care services to a patient, by providing health care providers with better and more efficient means for interacting with health plans and laboratories, including the ability to interact on mobile devices, such as mobile computing devices, including, for example, mobile phones, mobile tablets, and the like, would be advantageous.

SUMMARY

Embodiments of the present invention provide systems, methods, and media that may advantageously enhance the quality of health care related services to a patient, thereby enhancing patient care. Embodiments of the present invention also provide the advantages referenced above.

In an embodiment, the present invention provides systems, methods and media that present a health care provider with information to support a decision, for example, a decision relating to a test, or tests, for a patient. In addition, or in additional embodiment, the present invention provides systems, methods and media that present information relating to a patient's health plan to advantageously facilitate a health care provider's knowledge and use of a patient's health plan information. Further, or in an additional, or further, embodiment, the present invention provides systems, methods and media that present information relating to a laboratory to advantageously facilitate a health care provider's knowledge and use of laboratory information, including laboratory expertise. Still further, or in an additional, or still further, embodiment, the present invention provides systems, methods and media that advantageously allow interaction between and/or among a health care provider, a laboratory and/or a health plan.

In an embodiment, the present invention provides a system, a method or media that facilitates interaction among a health care provider and (i) a patient's information; (ii) a patient's health plan/health insurance information; and/or (iii) laboratory information. In an embodiment a system, a method or media of the present invention may present a health care provider with (i) a patient's medical information; (ii) a patient's health plan/health insurance information; and/or (iii) laboratory information to support a decision to be made by the health care provider.

As used herein health care provider refers to an individual or an institution that provides preventive, curative, promotional, or rehabilitative health care services to individuals, families or communities. An example of a health care provider includes, but is not limited to, a physicians, a physician's assistant, a nurse, a nurse's aide, a pharmacist, a pharmacist's assistant, a dentist, a dentist's assistant, a dental hygienist, a laboratory technician, a physical therapist, an occupational therapist and the like. As used in the present application, health care provider also includes administrative and other staff who may work with a health care provider.

As used herein, patient information may comprise medical information and refer to information relating to a patient's individual and/or family medical history, including but not limited to, physical characteristics such as height, weight, eye color, hair color, tattoo's, birthmarks; test information such as temperature, blood pressure, resting pulse, clinical test results; disease states past or present; pregnancy information; and similar information generally found in a health care record maintained by a health care provider and/or an insurer, and/or an electronic medical record.

As used herein, health plan, health insurance and/or health insurance plan, are used interchangeably to refer to a type of insurance coverage that pays for medical, surgical and/or laboratory expenses incurred by the insured. Examples of health plans in the US include government plans such as Medicare; Medicaid; Veterans Health Benefits; Active Duty Service Personnel Health Benefits; Federal Employees Health Benefits; and private, or semi-private, plans offered by companies such as UnitedHealth Group; Wellpoint, Inc. Group; Kaiser Foundation Group; Humana Group; HCSC Group; Coventry Corp. Group; Highmark Group; Blue Cross Blue Shield Group, and others. As used herein, health insurance and/or health insurance plan also includes employer self-insured plans.

As used herein Laboratory includes, for example, a diagnostic laboratory that provides diagnostic testing, information and services that patients and health care providers use to improve health care related decision-making by examining materials derived from the human body for the purpose of providing information on diagnosis, prognosis, prevention, or treatment of disease. Examples of diagnostic tests are set forth below and include, but are not limited to, blood tests, including total cholesterol, Pap testing and white blood cell count, pathological testing, including biopsy analysis, and molecular and/or genetic testing, that aid in the screening for, detection of and/or prognosis for and/or recover from disease states. As will be appreciated from the description herein, the foregoing definition is meant to provide a non-limiting general understanding of the nature and types of laboratories and laboratory tests that may be encompassed in embodiments of the present invention.

These illustrative embodiments are mentioned not to limit or define the invention, but rather to provide examples to aid understanding thereof. Illustrative embodiments are discussed in the Detailed Description, which provides further description of the invention. Advantages offered by various embodiments of this invention may be further understood by examining this specification.

BRIEF DESCRIPTION OF THE FIGURES

These and other features, aspects, and advantages of the present disclosure are better understood when the following Detailed Description is read with reference to the accompanying drawings, where.

DETAILED DESCRIPTION

Figure 1:
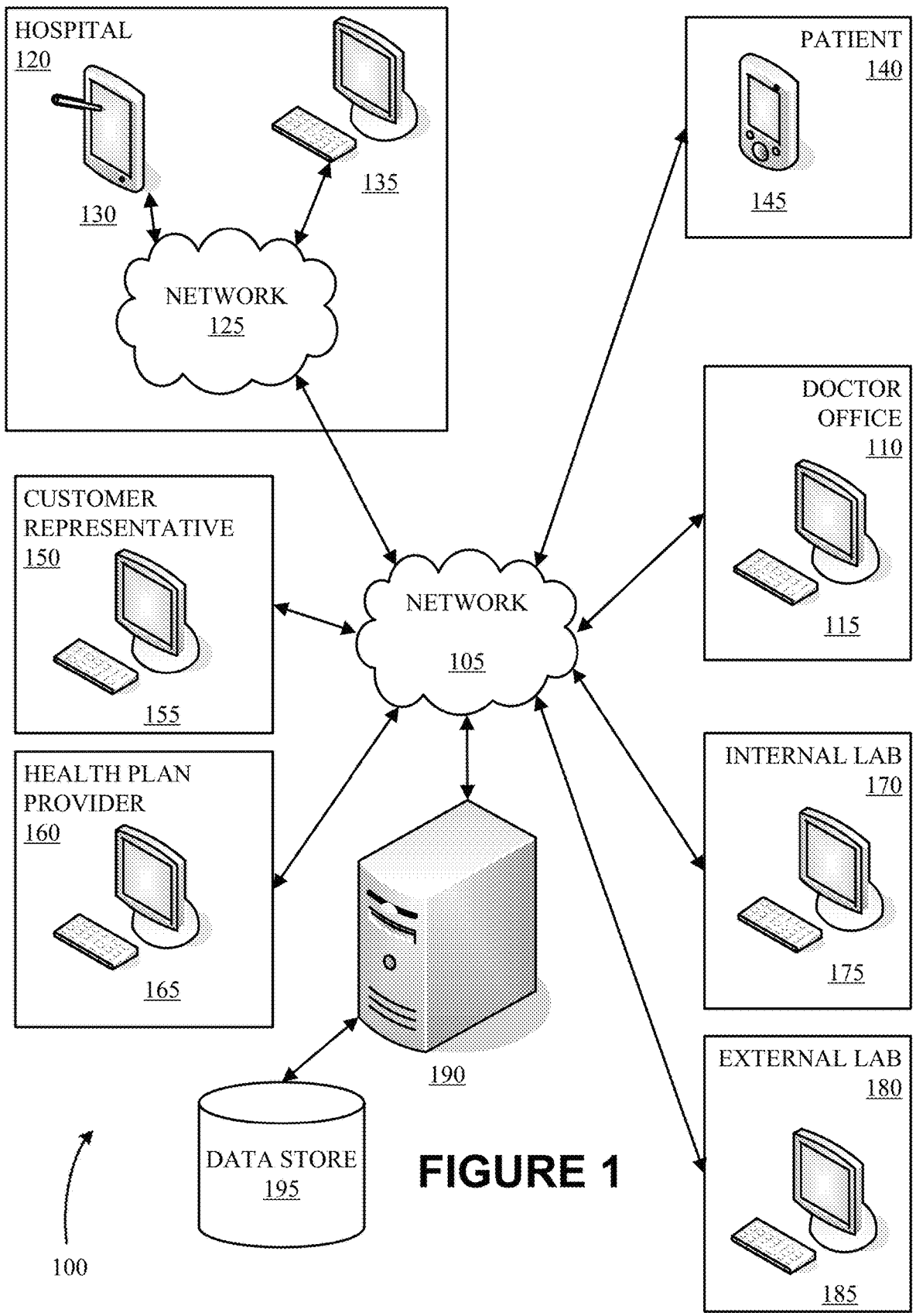
FIG. 1 is a system diagram depicting exemplary computing devices in an exemplary computing environment according to an embodiment.

Example embodiments are described herein in the context of a system, a method or media for presenting information to a health care provider to assist the health care provider in providing patient care. Those of ordinary skill in the art will realize that the following description is illustrative only and is not intended to be in any way limiting. Other embodiments will readily suggest themselves to such skilled persons having the benefit of this disclosure.

In an illustrative embodiment, a system of the present invention comprises:
 a computing device;
 at least one of: patient information; laboratory information; and/or health plan information; and
 a network in communication with the electronic device, the patient medical information, the laboratory information and/or the health plan information wherein at least one of the patient medical information, the laboratory information and/or the health plan information is accessible through the electronic device.

Suitable electronic devices include, but are not limited to, computer terminals, personal computers, tablets, smart phones and/or similar devices capable of providing information in a human readable format and receiving input from a human.

Patient information may comprise at least one datum from the data typically found on a patient's paper and/or electronic medical record, and/or a patient's paper and/or electronic health record relating to the patient's identification, physical characteristics, test results, medical conditions, medical history and/or care over time, and/or at least one datum related to a patient's current medical status or condition, including, but not limited to: a vital sign, including, but not limited to, body temperature, pulse rate (heart rate), blood pressure, respiratory rate, hemoglobin oxygen saturation and the like; intake: medication, fluid, nutrition, water and blood, etc.; output: blood, urine, excrement, vomitus, sweat, etc.; observation of pupil size; and/or capability of four limbs of body.

As understood by those of ordinary skill in the art, a patient's medical history may comprise a longitudinal record of what has happened to the patient since birth. For example, a patient's medical history may comprise information relating to diseases, major and minor illnesses, as well as growth landmarks. Medical history may include, but is not limited to, surgical history (a chronicle of surgery performed for the patient, dates of operations, operative reports, and/or the detailed narrative of what a surgeon did); obstetric history (prior pregnancies and their outcomes. It also includes any complications of these pregnancies); medications and medical allergies (a summary of the patient's current and previous medications as well as any medical allergies); family history (the health status of immediate family members as well as their causes of death (if known) and/or a list diseases common in the family or found only in one sex or the other and/or a pedigree chart); social history (a chronicle of human interactions, the relationships of the patient, his/her careers and trainings, schooling and religious training); habits (for example habits which impact health, such as tobacco use, alcohol intake, exercise and diet, and possibly sexual habits and sexual orientation); immunization history (history of vaccination and/or any blood tests proving immunity); growth chart and developmental history; medical encounters (discrete summations of a patient's medical history by a health care provider, e.g. a physician, nurse practitioner, or physician assistant using, for example a so-called SOAP (subjective, objective, assessment, and plan) including, for example, the chief complaint, history of the present illness, physical examination; assessment and plan); orders and prescriptions (orders by medical providers, including instructions given to other members of the health care team by a primary provider); progress notes (daily updates are entered into the medical record documenting clinical changes, new information, etc. often in the form of a SOAP note); laboratory test information (dates and results of testing, such as blood tests (e.g., complete blood count) radiology examinations (e.g., X-rays), pathology (e.g., biopsy results), or specialized testing (e.g., pulmonary function testing)); other information (including, but not limited to digital images of the patient, flowsheets from operations/intensive care units, informed consent forms, EKG tracings, outputs from medical devices (such as pacemakers), chemotherapy protocols, and the like).

Laboratory information may comprise at least one datum from data relating to a laboratory, for example a laboratory offering diagnostic testing, information and services that patients and health care providers use to improve health care related decision-making by examining materials derived from the human body for the purpose of providing information on diagnosis, prognosis, prevention, or treatment of disease. The data relating to a laboratory may include, but is not limited to, data relating to: test offerings, expertise, location, contact information, processing time, sample collection, insurance reimbursement, insurance network coverage, as well as detailed information relating to specific tests and the relationship between published medical and/or scientific literature and a test or tests, and/or specific medical conditions.

Health plan information may comprise at least one datum from data relating to a health plan and/or a health insurance plan including, but not limited to, benefit information, coverage information, co-pay information, reimbursement information, claim information, claim processing time, test approval information, frequently asked questions, contact information and/or similar information relating to patient coverage.

A network comprises a plurality of computing devices, including, but not limited to, computers, personal computers, mini-computers, mainframes, tablets, smart phones, storage devices (e.g. RAID devices), and similar hardware, interconnected by communication channels that allow sharing of resources and information. The communication channels may be wired or wireless. Communication protocols define the rules and data formats for exchanging information in a computer network, and provide the basis for network programming. Typical communications protocols include two Ethernet, a hardware and link layer standard that is ubiquitous in networks, and the Internet protocol suite, which defines a set of protocols for internetworking, i.e. for data communication between multiple networks, as well as host-to-host data transfer, and application-specific data transmission formats. In an embodiment of the present invention, a network may: facilitate communication; permit sharing of files, data and other types of information; allow a user, e.g. a health care provider, to access information stored on other computers on the network; allow a user, e.g. a health care provider to share computing resources; and/or provide other features.

In an embodiment of the present invention, a database, or a plurality of databases, may comprise patient information data, laboratory information data acid/or health plan information data. The database, or plurality of databases, may be located on a single computing device or a plurality of computing devices. In an embodiment, a laboratory computing device comprises laboratory information data and/or health plan information data. In another embodiment, a health plan computing device comprises health plan information data, patient information data and/or laboratory information. In another embodiment, a health care provider computing device comprises patient information data, health plan information data and/or laboratory information data. In another embodiment, a service provider computing device aggregates, and/or provides links to health care provider, health plan and/or laboratory computing devices, comprising patient information data, laboratory information data and/or health plan information data.

In an illustrative embodiment, a method of the present invention comprises: presenting a health care provider with at least one of: patient information; laboratory information; and/or health plan information; to assist the health care provider with a decision. A system of the present invention may be utilized to perform a method of the present invention, however a method of the present invention may also be performed using other components.

The process of presenting a health care provider with at least one of patient information; laboratory information; and/or health plan information may comprise presenting the information on a computing device. In an embodiment, a health care provider may access at least one of patient information; laboratory information; and/or health plan information using a computing device. The process may further comprise receiving input from the health care provider. The input may comprise new or additional patient information, for example data relating to relatively current patient condition. The input may in addition, or further, comprise input necessary to be granted access to patient information, laboratory information and/or health plan information, for example log-on information for a database comprising the information.

In another illustrative embodiment, a method of the present invention comprises: receiving input from a health care provider relating to a patient condition and generating output to present to the health care provider based on at least one of: patient information; laboratory information and/or health plan information. A system of the present invention may be utilized to perform a method of the present invention, however a method of the present invention may also be performed using other components.

The process of receiving input from a health care provider may comprise a health care provider providing data relating to a relatively current patient condition. The input may be provided directly by the health care provider, and/or the input may be made to a patient medical record and comprise patient information.

The process of generating output to present to the health care provider may comprise use of a policy, such as the policies detailed below. A policy may use patient information, laboratory information and/or health plan information to determine output to present to the health care provider. A policy may comprise evidence based guidelines. Evidence based guidelines may comprise systematically developed statements designed to assist health care providers, health plans and patients make informed decisions about appropriate health care for specific circumstances. Evidence based guidelines may be developed by professional societies, medical professionals, scientists, health plans, government panels, patient groups and/or cooperative groups. For health care providers, evidence based guidelines may provide a summary of the relevant medical literature and present options relating to which diagnostic tests to order, which treatments to use for specific conditions and/or other aspects of clinical practice.

In an embodiment of the present invention output may comprise laboratory information and/or health plan information, and may further comprise options for patient care. By way of a non-limiting example, output may present a health care provider with an option and/or options for a diagnostic test, a laboratory qualified to perform the diagnostic test and/or plan coverage information from a patient's health plan relating to coverage for the diagnostic test. Output may advantageously assist and/or support a health care provider's decision making.

Reference will now be made in detail to implementations of example embodiments as illustrated in the accompanying drawings. The same reference indicators will be used throughout the drawings and the following description to refer to the same or like items.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Operation

In one embodiment, a health care provider uses an electronic device to access a website for to access patient information, laboratory information and/or health plan information. The health care provider can use the electronic device to determine one or more possible laboratory tests through the website. For example, the health care provider can use the electronic device to select or send medical information—such as one or more medical classification codes, symptoms, diseases, historical medical information for a patient, etc.—to a server. In response to receiving the medical information, the server can determine one or more possible laboratory tests. For example, the server may use the received medical information to query a data store comprising a plurality of laboratory tests to determine one or more possible laboratory tests. The determined one or more possible laboratory tests can be based at least in part on the received medical information. At least one of the determined possible laboratory tests can be sent to the electronic device by the server.

In some embodiments, a health care provider can use the electronic device to order one or more laboratory tests through the website. For example, the server may send five possible laboratory tests to the electronic device in response to receiving a list of symptoms from the electronic device. In this embodiment, a health care provider can select one or more of the possible laboratory tests and submit an order for the selected tests through the website. In one embodiment, the server receives an order for one or more laboratory tests from the electronic device and provides one or more additional and/or alternative laboratory tests. For example, a server may query a data store to determine an alternative laboratory test to recommend for an order for a particular laboratory test. An alternative laboratory test may be based on factors such as evidence based guidelines, patient eligibility, historical medical information, and/or other factors. As another example, an additional laboratory test may be recommended if factors indicate that an additional laboratory test may need to be ordered. Thus, in one embodiment, evidence based guidelines may suggest that an additional laboratory tests should be ordered when a particular laboratory test is ordered. Numerous other embodiments are disclosed herein and variations are within the scope of this disclosure.

This illustrative example is given to introduce the reader to the general subject matter discussed herein. The invention is not limited to this example. The following sections describe various additional non-limiting embodiments and examples of devices, systems, and methods for laboratory testing management.

Illustrative System

FIG. 1 is a system 100 diagram depicting exemplary computing devices in an exemplary computing environment according to an embodiment. The system 100 shown in FIG. 1 includes a network 105 in communication with various devices associated with health care providers, e.g. doctor offices 110, hospitals 120, patients 140, customer representatives 150, which may comprise health care provider customer representatives, laboratory customer representatives, and/or health plan customer representatives, health plan providers 160, internal labs 170, and external labs 180. The various devices that network 105 is in communication with include, but are not limited to, a desktop computer (e.g. 155), a tablet computer (e.g. 130), or a mobile phone (e.g. 145). The network 105 in FIG. 1 is also in communication with a server 190 and the server 190 is in communication with a data store 195. The network 105 may be in communication with other networks such as, for example, network 125 which associated with the hospital 120. In embodiments, the various devices can send and receive messages with other devices associated with network 105. Thus, a desktop computer 115 in the doctor's office 110 is to communicate with server 190 through the network 105. As another example, a desktop computer 175 associated with an internal laboratory 170 may be able to receive information from data store 195 or store information to data store 195, or both, through the network 105 and the server 190.

In embodiments, various devices including, but not limited to, desktop computer 115, tablet computer 130, and mobile phone 145, may be any device capable of communicating with a network, such as network 105, and capable of sending and receiving information to and from another device. For example, in FIG. 1, one device may be a tablet computer 130. The tablet computer 130 includes a touch-sensitive display and capability of communicating with network 105 through network 125 for example through the use of a wireless network interface card. Another device shown in FIG. 1 is a desktop computer 115. The desktop computer 115 has a display and is connected to network 105 through a wired network connection. The desktop computer 115 may be in communication with any number of input devices such as a keyboard or a mouse. In various embodiments, tablets, desktop computers, or other suitable computing devices may be associated with one or more health care providers, patients, customer representatives, health plan providers, internal labs, external labs, or other users.

In embodiments, network 105 shown in FIG. 1 facilitates communications between the various devices (i.e. 145, 155, 175, 185, etc.) and server 190. The network 105 may be any suitable number or type of networks or links, including, but not limited to, a dial-in network, a local area network (LAN), wide area network (WAN), public switched telephone network (PSTN), the Internet, an intranet or any combination of wired and/or wireless communication links. In one embodiment, the network 105 may be a single network. In other embodiments, the network 105 may comprise two or more networks. For example, the various devices may be connected to a first network, such as network 125, and the server 190 may be connected to a second network, such as network 105, and the first and the second network may be connected. Numerous other network configurations would be obvious to a person of ordinary skill in the art.

In embodiments, network 125 shown in FIG. 1 facilitates communications between the various devices (i.e. 130, 135, 145 etc.) and server 190. The network 125 may also be any suitable number or type of networks or links, including, but not limited to, a dial-in network, a local area network (LAN), wide area network (WAN), public switched telephone network (PSTN), the Internet, an intranet or any combination of wired and/or wireless communication links. In one embodiment, the network 105 may be a single network. In other embodiments, the network 105 may comprise two or more networks. For example, various devices may be connected to a first network, such as network 125, and the server 190 may be connected to a second network, such as network 105, and the first and the second network may be connected.

In FIG. 1, network 125 is associated with hospital 120. In embodiments, any number of entities may be associated with one or more networks. For example, a network associated with customer representative 150 may be in communication with network 105. Likewise, a network associated with an external laboratory 180 may be associated with network 105. Numerous other networks associated with entities—such as a doctor's office 110, a health plan provider 160, patient 140, or internal laboratory 170—and connected with network 105 may be present in various embodiments. Other network configurations would be obvious to a person of ordinary skill in the art.

In some embodiments, communication between devices, networks, or entities, or some combination thereof, may be facilitated by the Internet. For example, network 105 may be in communication with network 125 through the Internet. In some embodiments, such communication may be secure. For example, a hypertext transfer protocol secure (HTTPS) may be used to provide encrypted communication between various devices, networks, or entities, or some combination thereof. In another embodiment, a virtual private connection (VPN) may be used to provide communication. For example, a gateway associated with network 125 can be in communication with a gateway associated with network 105 through a VPN connection. In one embodiment, a VPN connection may contain a single tunnel connection. To at least provide redundancy, however, a VPN connection may comprise two or more tunnel connections. Thus, if one tunnel connection in the VPN connection fails, communication may still be successful through the other tunnel connection.

The server 190 shown in FIG. 1 may be any device capable of communicating with a network, such as network 105, and capable of sending and receiving information to and from another device. For example, in the embodiment shown in FIG. 1, the server 190 may receive a request from various devices such as tablet computer 130, desktop computer 155, or other devices. In this embodiment, the server 190 may respond to the request by sending information back to the requesting device through the network 105. Thus, if server 190 receives a request from desktop computer 115 associated with doctor office 110 through network 105, then the server 190 may process the request including performing any necessary communication with any other device and respond to the request by sending a response back to the desktop computer 115 through the network 105. In an embodiment, the server 190 can communicate with a gateway associated with the server and network 105. The server 190 may be in communication with one or more data stores, such as data store 195.

In embodiments, server 190 may be in communication with one or more additional devices, such as additional servers. In some embodiments, server 190 may communicate with one or more additional devices to process a request received from another device. For example, the server 190 in FIG. 1 may be in communication with a plurality of additional servers, at least one of which may be used to process at least a portion of a request received from another device, such as tablet computer 130, or desktop computer 175. In other embodiments, the server 190 may send a request to one or more devices and process any response received from the device or devices. For example, server 190 may send a request to desktop computer 135 associated with hospital 120. In this embodiment, the server 190 may receive a response from the desktop computer 135 and process the response. For example, the server 190 may store information related to the response in data store 195.

The system 100 shown in FIG. 1 includes a data store 195. The data store 195 can include numerous separate data stores, data tables, databases, or other data storage mechanisms and media for storing data relating to particular aspects of one or more of the embodiments disclosed herein. The architecture depicted in FIG. 1 is merely illustrative, and embodiments may be implemented using various different architectures.

Figure 2:
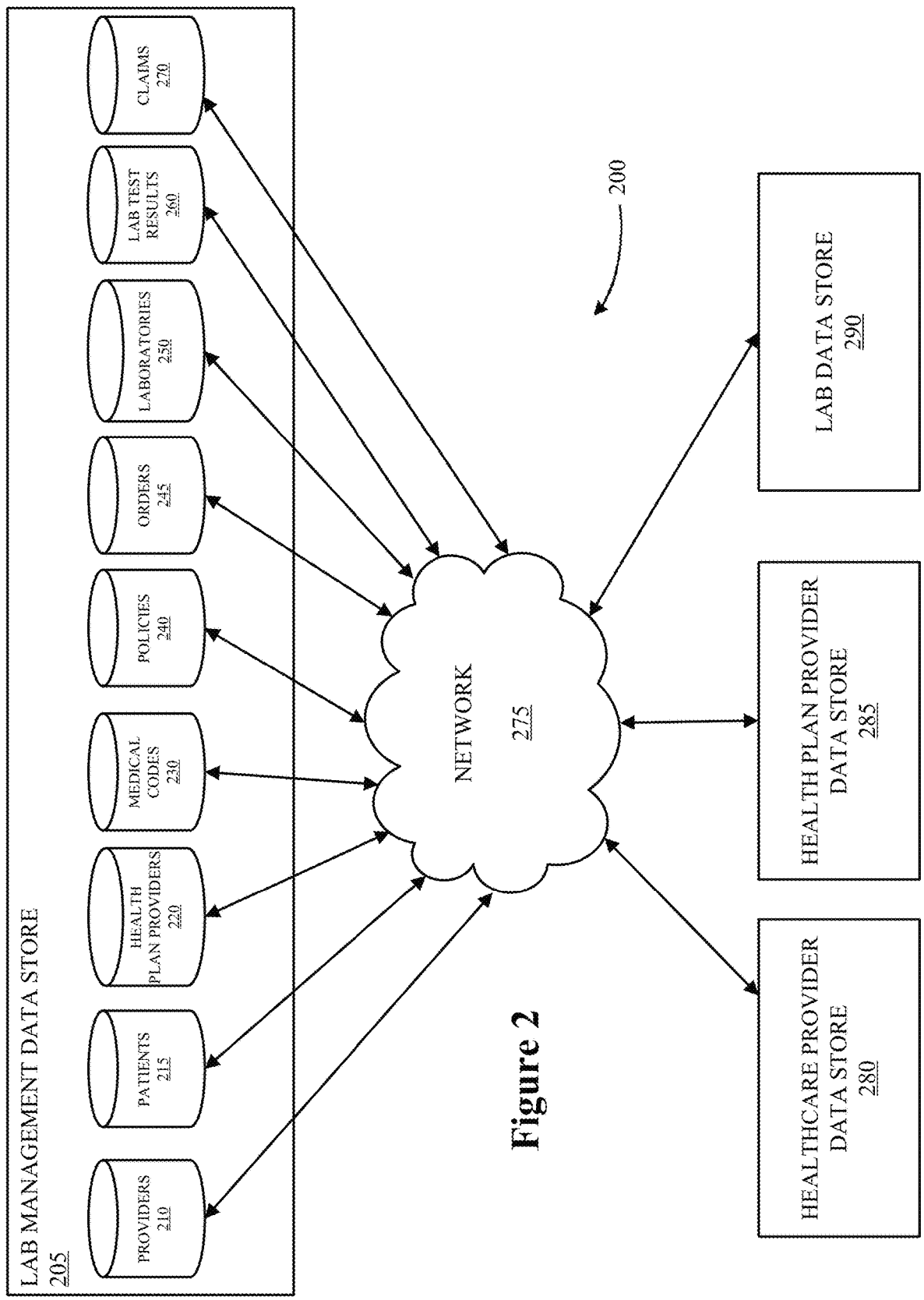
FIG. 2 is a flow chart illustrating an example of a system 200 comprising various data stores that can store information according to an embodiment.

FIG. 2 is a flow chart illustrating an example of a system 200 comprising various data stores 205, 280-290 that can store information according to an embodiment. In the system 200 shown in FIG. 2, a laboratory management data store 205, a health care provider data store 280, a health plan provider data store 285, and a laboratory data store 290 are in communication with each other through network 275. Information stored in a data store may be accessed by one or more other data stores. For example, information stored in the health plan provider data store 285 may be accessed by the laboratory management data store 205. In embodiments, information stored in the laboratory management data store 205 may be accessed by the health plan provider data store 285. Information may be sent to or saved by, or both, one or more data stores from another data store. For example, information regarding a laboratory testing order may be sent by the health care provider data store 280 through network 275 the laboratory management data store 205. In this embodiment, the laboratory management data store 205 may store laboratory testing order data to the orders database 245. In another embodiment, information regarding the results of a laboratory test may be sent from laboratory management data store 205 to health care provider data store 280. In various embodiments, information stored in data stores 205, 280, 285, and 290 may contain information stored in data store 195 shown in FIG. 1 according to various embodiments.

In embodiments, network 275 shown in FIG. 2 facilitates communications between the various data stores 205, 280, 285, and 290. The network 105 may be any suitable number or type of networks or links, including, but not limited to, a dial-in network, a local area network (LAN), wide area network (WAN), public switched telephone network (PSTN), the Internet, an intranet or any combination of wired and/or wireless communication links. In one embodiment, the network 105 may be a single network. In other embodiments, the network 105 may comprise two or more networks. For example, the various devices may be connected to a first network, such as network 125, and the server 190 may be connected to a second network, such as network 105, and the first and the second network may be connected. Numerous other network configurations would be obvious to a person of ordinary skill in the art.

In the embodiment shown in FIG. 2, the laboratory management data store 205 comprises information related to various aspects of a laboratory management system. The laboratory management data store 205 in FIG. 2 comprises information related to health care providers 210. For example, information related to health care providers 210 can include names, addresses, phone numbers, personnel, usernames, passwords, other security information, access levels, and other information associated with one or more providers. The laboratory management data store 205 in FIG. 2 contains information related to patients 215. Information related to patients 215 may include patient names, addresses, telephone numbers, providers to which the patients are associated, medical history, medications, relatives, health care provider plans, account balances, access information, or other information related to one or more patients.

In FIG. 2, the laboratory management data store 205 includes information related to health plan providers 220. For example, information related to health plan providers can include insurance companies, various insurance plans, payment information for laboratory tests, information related to one or more patients, deductible information, testing notification data, or other information associated with one or more health plan providers. The laboratory management data store 205 in FIG. 2 comprises information related to medical codes 230. Such information may include medical classifications for diseases, signs, symptoms, potential causes of injury, potential causes of one or more diseases, testing procedures, laboratory tests, other coding information, or a combination thereof. For example, in one embodiment, information related to medical codes 230 can include data from the International Statistical Classification of Diseases and Related Health Problems (ICD) such as the ICD-9 medical classification list or the ICD-10 medical classification list. In another embodiment, information related to medical codes 230 may include data such as the American Medical Association's (AMA) CPT data code files that provide at least a list of CPT procedural codes.

The laboratory management data store 205 in FIG. 2 contains a policy or polices 240. A policy may comprise evidence based guidelines for one or more diseases, illnesses, medical tests, etc. In one embodiment, information related to policies 240 includes information that may be used to offer suggestions regarding tests or procedures that are typically followed for a particular illness, system or set of symptoms, or other evidence-based information. In one embodiment, a set of questions related to one or more policies, illnesses or one or more symptoms may be stored in data base 240. The laboratory management data store 205 in FIG. 2 includes information related to orders 245. For example, information related to orders 245 can include information related to health care providers that have placed an order, information related to patients for which an order has been placed, information related to the tests that have been performed, billing information, payment information, accounts receivable information, order status, one or more laboratories associated with orders, test results, or a combination thereof.

The laboratory management data store 205 in FIG. 2 comprises information related to laboratories 250. For example, a laboratories database 250 may contain information such as location, costs for various tests, turnaround time, type of tests performed, current capacity levels, historical information related to tests that have been performed by one or more laboratories, current information regarding one or more orders such as order statuses, addresses, personnel, contacts, usernames, passwords, other identification, or other laboratory information. In embodiments, the laboratories database 250 may contain information to distinguish internal laboratories from external laboratories. Internal laboratories can include laboratories owned by or affiliated with one or more organizations operating a laboratory benefits management system. For example, if an organization is operating the laboratory benefits management system described herein and the organization owns a laboratory, in one embodiment, the laboratory can be considered an internal laboratory. Examples of external laboratories can include laboratories not owned or operated by an organization operating the laboratory benefits management system. For example, in one embodiment, an organization may own several laboratories, but none of the internal laboratories perform a particular test that has been ordered. In this embodiment, the laboratories database 250 may contain information for an external laboratory that has the capability to perform the test. Numerous other embodiments or additional information that may be stored in the laboratories database 250 will be obvious to one of skill in the art.

The laboratory management data store 205 in FIG. 2 contains information related to laboratory test results 260. Information related to laboratory test results 260 can include information such as the actual results of the test, suggested follow-up tests, historical information based on past test results, diagnostic information, information related to medical guidelines or thresholds for one or more tests, and other information related to test results. The laboratory management data store 205 in FIG. 2 includes information related to claims 270. For example, information related to claims can include the payment status for claims, whether the claim has been submitted to a health plan provider, eligibility verification information, benefits determination information, whether a claim requires editing, whether the claim needs or has been adjusted, or other information related to one or more claims.

In various embodiments, information stored in data stores 205, 280, 285, and 290 may contain information stored in data store 195 shown in FIG. 1 according to various embodiments. It should be understood that there can be many other aspects that may need to be stored in data stores 205, 280, 285, or 290, or some combination thereof. In various embodiments, information shown in data store 205 may be stored in any number of data stores including, but not limited to, data store 280, 285, or 290. In some embodiments, data store 205 may access or store information, or both, in one or more data stores, such as data store 280, 285, or 290. For example, in one embodiment, data store 290 may contain laboratory test results 260. In this embodiment, data store 205 may be able to access information or store information related to laboratory test results 260 by accessing data store 290 through network 275. One or more data stores may be associated with any number of entities. For example, data store 280 may be associated with a health care provider such as a hospital or a doctor's office. In one embodiment, data store 280 may be associated with a hospital and one or more satellite braches such as other facilities located in surrounding communities. In other embodiments, data store 280 may be associated with multiple hospitals or other facilities owned, affiliated with, or related to one another. Data store 285 may be associated with a health plan provider such as an insurance company. Data store 290 may be associated with one or more labs such as an internal laboratory or an external laboratory. It should be understood that information may be stored in any appropriate mechanisms or in additional mechanisms in one or more of data stores 205, 280, 285, or 290.

Referring back to FIG. 1, data store 195 is operable, through logic associated therewith, to receive instructions from various devices—such as server 190, other data stores, networks 105 or 125, other devices (i.e. 130, 145, 175, etc.), or a combination thereof—and obtain, update, or otherwise process data in response thereto. As one example, a doctor's office 110 may obtain laboratory information using desktop computer 115 to the server 190 through network 105. In this case, the server 190 may process the order at least by querying the data store 195 to verify the identity of the doctor's office and, if the doctor's office is authorized, process the request for information. It should be understood that there can be many other aspects that may need to be stored in the data store 195, such as page image information or access rights information, which can be stored in any appropriate mechanisms or in additional mechanisms in the data store 195.

In FIG. 1, numerous entities, such as hospital 120 and internal laboratory 170, are shown. In various embodiments, any number of entities may be associated with network 105 or can send information to server 190 or receive information from server 190, or some combination thereof. In the embodiment shown in FIG. 1, health care providers, including hospital 120 and doctor office 110, health plans, laboratories, as well as patient 140 are in communication with network 105. A health care provider can be any personnel or facility that provides health care services to one or more patients. A patient can be anyone who receives treatment from a health care provider. In FIG. 1, a customer representative 150 is in communication with network 105. In embodiments, a customer representative 150 may be one or more companies or individuals that provide support to patients 140 or entities (i.e. hospital 120, internal laboratory 170, health plan provider 160, etc.), or both. For example, a health care provider 160 may call a customer representative 150 to verify the status of a laboratory test that was ordered for a patient, and/or to obtain benefit information based on patient information, laboratory information and/or health provider information. Numerous entities may be in communication with network 105, additional networks, other entities, or additional devices according to various embodiments of the present invention.

The environment in an embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 1. Thus, the depiction of the system 100 in FIG. 1 should be taken as being illustrative in nature, and not limiting to the scope of the disclosure.

In an embodiment the present invention comprises a web portal. The web portal may be horizontal or vertical, or a combination of a horizontal portal and a vertical portal. A health care provider may access patient information, health plan information and/or laboratory information through the portal. In an embodiment, a health care provider may be presented with a single web page that brings together and/or aggregates content from other systems and/or servers, and/or a database, or databases, that include patient information, health plan information and/or laboratory information. A web portal may also be configured to provide an embodiment or embodiments of application functionality described herein (e.g. to perform a method of the present invention). In this type of embodiment the web portal may be hosted on a portal server that includes connectivity to an application server.

By way of example, Service-Oriented Architecture (SOA) is one example of how a portal can be used to deliver application server content and functionality. The application server or architecture performs the actual functions of the application. This application server is in turn connected to database servers, and may be part of a clustered server environment. High-capacity portal configurations may include load balancing equipment. SOAP, an XML-based protocol, may be used for servers to communicate within this architecture. The server hosting the portal may only be a "pass through" for the user. By use of portlets, application functionality can be presented in any number of portal pages. For the most part, this architecture is transparent to a user.

Illustrative Operation and Method

An example of the operation of a laboratory benefit management system according to an embodiment of a method is set forth below. The example will be described with respect to the environment shown in FIG. 1.

A method begins when a patient visits a health care provider. For example, referring to FIG. 1, the patient 140 may visit a health care provider physician at a doctor's office 110. Once the patient visits the health care provider 110, the health care provider reviews patient information, and may input additional patient information, for example in conjunction with an examination of the patient. For example, referring to FIG. 1, the physician at the doctor's office 110 may determine that the patient's current symptoms and medical history. The physician could access an embodiment of the present invention through a web portal on a computing device, 115. The physician could access patient information through the web portal and could also access health plan information and/or laboratory information. The physician, and/or another health care provider, may also input new patient information, including the patient's medical condition through the web portal. The patient information, including updated patient information, health plan information and laboratory information are received and/or accessed.

Patient information and/or health plan information may be reviewed, input and/or communicated by any number of persons. For example, referring to FIG. 1, personnel in the doctor's office 110 may review, input and/or communicate medical information, e.g. through a portal. In embodiments, a physician, a nurse, an administrative assistant, other office personnel, or other persons associated with a health care provider may may review, input and/or communicate patient information and/or health plan information through one or more electronic devices, such as devices 130, 135, 115 shown in FIG. 1 or another suitable electronic device. For example, a physician, a physician's assistant and/or a nurse may review and/or input patient information, such as one or more current symptoms for a patient, and communicate patient information via an electronic device and the physician, physician's assistant and/or a nurse may be presented with laboratory test options on the electronic device in view of the communication. In another embodiment, a physician, a physician's assistant and/or a nurse physician may communicate patient information and a desired laboratory test via an electronic device and the physician, physician's assistant and/or nurse may be presented with one or more alternatives for additional and/or replacement laboratory tests based at least in part on the received communication.

Patient and/or health plan information may be sent in any number of ways. In one embodiment, personnel associated with a health care provider may use one or more devices to electronically send information to an organization. For example, referring to FIG. 1, a nurse associated with doctor's office 110 may use desktop computer 115 to send an email to a laboratory benefits organization associated with server 190 and the email may contain patient and/or health plan information. In another embodiment, a person communicating patient information and/or health plan information may visit a website designed to receive the information. For example, referring again to FIG. 1, a doctor may visit a website associated with a laboratory benefits organization using desktop computer 115 by sending a request to server 190 through network 105. In response to the request, the server 190 may send a response to the desktop computer 115 through network 105. The website may contain one or more security measures, such as requiring a username and password or a digital certificate, to verify the authenticity of the doctor submitting the information. For example, the server 190 may access data store 195 to determine whether information received from the desktop computer 115 associated with the doctor's office 110 successfully authenticates a user of the desktop computer 115. In this embodiment, once the authenticity of the doctor has been verified, the website may contain one or more forms that the doctor can fill out to input patient information for one or more patients. In another embodiment, patient and/or health plan information may be received by server 190 from various devices through an application programming interface (API) call. In various embodiments, one or more applications, such as a desktop application or a Windows®-based application, associated with the health care provider may be executed that facilitates submitting patient and/or health plan information. For example, tablet computer 130 associated with hospital 120 may contain an application that can be executed by a user to submit information to a laboratory benefits service organization. The application may be able to communicate with other devices, such as server 190, through network 105 and network 125.

When a device, such as tablet computer 130 or desktop computer 115, sends/accesses patient information and/or health plan information, another device may receive the information. For example, if an administrator at hospital 120 uses tablet computer 130 to send/access information, then server 190 may receive the information through network 105 and network 125. In embodiments, a device receiving the information may process the request. For example, if server 190 receives information from desktop computer 115, then server 190 may process the received information.

Processing the information may comprise determining a patient's eligibility for health plan benefits using patient information and/or health plan information. Processing may further comprise comparing patient information and/or health plan information to a database to determine patient eligibility. In an embodiment, processing the information may further comprise analyzing patient information, health plan information, and/or laboratory information and presenting the submitter of the information, e.g. a health care professional, with options for at least one of a laboratory test and/or a laboratory facility based on the information. 360. In an embodiment, processing information comprises comparing information to a policy or policies and presenting the information submitter, e.g. a health care professional, with options based on patient information, health plan information and/or laboratory information. A policy is described in further detail below.

In an embodiment, a device sending information and a device receiving information may send and receive information back and forth to present a health care provider, or another user of the system, e.g. a health plan provider, with alternatives, including alternative laboratory tests, and/or alternative laboratories. The laboratories presented may be selected on any number of criteria, including but not limited to, health plan benefit information, laboratory expertise with a test or tests, laboratory processing time, laboratory fee information, and similar information used by health care providers and/or health plan providers to select a laboratory for diagnostic testing.

In an embodiment the processing of information may comprise determining a need for additional information. For example, if patient information is in some way incomplete then the processing device may request additional information by calling out to the submitting device. By way of a non-limiting example, a particular laboratory test may be not be offered to a pregnant woman and the patient information submitted to the processing device may lack information relating to whether the woman is currently pregnant. In processing the information the processing device may call out with a request that the patient's pregnancy status be included in patient information, for example through health care provider input of the status. By way of another non-limited example, a policy for a particular laboratory test may suggest a prerequisite laboratory test. The processing device may call out with a request that information relating to the prerequisite test be included in patient information, for example through health care provider input, or through a comparison to historical patient information maintained in a database. Those of ordinary skill in the art will recognize that there are many additional examples of information that may be desired in processing. As noted herein, processing may also comprise determining a patient's eligibility for health plan benefits using patient information and health plan information. The foregoing examples may also relate to information desired to determine a patient's eligibility for health plan benefits.

Information may be sent back and forth between a health care provider's computer and a computer associated with the laboratory benefits system. For example, as a health care provider communicates symptoms of a patient, for example as part of patient information, this information may be sent to the computer associated with the laboratory benefits system. In an embodiment, a server associated with the laboratory benefits system may process patient information, health plan information and laboratory information in view of a policy and communicate a possible diagnostic test option and/or options; a laboratory and/or laboratories; and/or health plan benefit information for presentation to the health care provider. In an embodiment, information generated by processing, for example processing with respect to a policy or policies, may be communicate to a patient, for example through a patient device in communication with the network; a health plan provider, for example through a health plan provider device in communication with the network and/or a laboratory, for example through a laboratory device in communication with the network. Thus, in an embodiment, a system or method of the present invention facilitates information flow among parties involved in providing patient care.

In an embodiment, information may be received that contains one or more tests for one or more patients to be ordered. In another embodiment, information may contain present or historical, or both, information related to one or more patients and this information may be used in processing with reference to a policy or policies to determine one or more recommended tests. Information can include current and/or past medical statistics, current and/or past biographical information, current and/or past laboratory orders, current and/or past laboratory results, current and/or past symptoms, current and/or past diagnoses, current and/or past treatments, current and/or past prescriptions, current and/or past indications, current and/or past health care providers, current and/or past insurance providers, medical codes such as ICD-9 codes, other medical information, or a combination thereof. Numerous other embodiments or implementations, or both, will be obvious to one of skill in the art or are disclosed herein.

As noted herein, once medical information has been received, the information may be processed. The processing may occur through a decision support component. Physician decision support may present a physician with options, for example options for laboratory tests for a patient, based on patient information, health plan information and/or laboratory information. For example, if processing patient information suggests an illness, frequently ordered laboratory tests for that illness may be presented. If the information includes information relating to one or more laboratory tests and/or laboratory test results, processing may result in presenting additional laboratory tests. The one or more additional laboratory tests can be presented on the received patient information, health plan information and/or laboratory information, medical information for a patient, past medical information for a patient, medical information for a population of patients, evidenced-based medical guidelines, information corresponding to one or more laboratories, information corresponding to one or more health care providers, information corresponding to one or more insurance providers, information corresponding to one or more laboratory system management providers, other medical information, or a combination thereof. In one embodiment, if the information comprises an order for one or more laboratory tests, processing may result in the presentation of one or more alternative laboratory tests.

Information provided, and/or decision support information, may be accessed, collected, and/or verified. For example, information contained in a request may be verified against one or more medical classification lists such as ICD-9, ICD-10, or CPT data. In one embodiment, a policy comprising evidence based guidelines may be used to determine one or more laboratory tests—including, but not limited to, additional and/or alternative laboratory tests if the received information includes an order for one or more laboratory tests—for one or more patients associated with the received information. For example, information related to a patient's medical history may be accessed and used to determine whether one or more additional or alternative tests for the patient may be presented based at least in part on one or more evidence based guidelines. Similarly, information related to a patient's symptoms may be contained in the information or otherwise accessed and used to determine whether one or more laboratory tests for the patient or patients can be recommended based at least in part on one or more evidence based guidelines. In some embodiments, a patient's medical history, past symptoms, present symptoms, or a combination thereof, may be used to determine one or more laboratory tests. For example, received information may comprise a patient's current symptoms which are used to determine one or more suggested laboratory tests for the patient. In one embodiment, information comprises symptoms as well as a laboratory test for a patient and the symptoms are used, at least in part, to determine one or more additional or alternative tests for the patient. Other information, such as a patient's medical history, may be used in connection with a patient's symptoms to determine one or more tests to be presented.

Processing may also be used to determine a patient's health plan eligibility and benefits for the one or more laboratory tests to be performed. Patient eligibility and benefits may be determined in any number of ways. In one embodiment, patient eligibility and benefits are verified using information contained in one or more data stores. In another embodiment, server 190 may query one or more external data stores, such as health plan provider data store 285 shown in FIG. 2, to make a determination as to whether a patient 140 is eligible and what benefits patient 145 should receive. In embodiments, various records may be kept regarding one or more orders or laboratory tests. For example, records may be kept regarding responsible payor or payors, an amount owed, addresses, one or more statuses of an order, etc. Variations are within the scope of this disclosure and will be apparent to one of skill in the art. As noted herein, eligibility information may be included in information presented to a health care provider and/or other users.

Processing may in addition, or in the alternative, include processing of laboratory information, health plan information and/or patient information to develop an option or options for a laboratory or laboratories to perform a test, e.g. a test requested by a health care provider and/or a test presented to a health care provider though the processing described herein with reference to a policy or policies. In an embodiment, processing may present options for one or more laboratories to perform at least a portion of a test. Such a determination may be based on any number of factors. For example, a determination may be based on a timeframe for completing at least a portion of the order. In this embodiment, a laboratory that has the capacity to provide laboratory results for the portion of the order may be selected. For example, if an order specifies a particular laboratory test and ten laboratories are available to complete the laboratory test, then the laboratory with the overall lowest cost for performing the laboratory test may be chosen. A determination can be based on other factors such as location of the laboratory, whether the laboratory is an in-network or out-of-network laboratory, whether the laboratory is owned or operated by the laboratory benefits organization, or other factors. Numerous various are disclosed herein and others will be apparent to one of skill in the art.

Processing may also include processing laboratory information comprising status of an order; laboratory results; laboratory reimbursement; and/or other items of interest to a health care provider, patient, health plan provider and/or laboratory. Information on these, or similar, items may be presented to a health care provider for review. For example, if an external laboratory is selected to perform a laboratory test, the status of the laboratory test may be tracked. The status of the laboratory test may include information such as whether a sample related to the test has been collected, the historical location of the sample, a current location of the sample, whether the laboratory test has been started, an expected completion date for the laboratory test, whether the results of a laboratory test are available, whether the results of a laboratory test have been received, or other status information. In embodiments, status information may be exchanged between various devices. For example, referring to FIG. 1, an internal laboratory 170 may send status information to server 190 through network 105 which is stored in data store 195. In one embodiment, status information may be sent from server 190 to an external laboratory 180 through network 105.

As noted above, various entities may be able to access at least some information regarding a laboratory test. For example, a physician or other personnel in doctor's office 110 may be able to view the status of one or more laboratory tests. A physician may be able to view the results of one or more laboratory tests. In one embodiment, a health care provider can customize the presentation of results of one or more laboratory tests. For example, one health care provider may customize test results so that only raw data related to the laboratory test is sent in the test results. Another health care provider may customize test results so that raw data as well as graphical indications, such as a bar chart or a pie chart, is shown in a test results report. In another embodiment, the health care provider can customize the test results report to include historical medical information related to one or more patients. In yet another embodiment, the health care provider can customize test results reports to include one or more recommendations based at least in part on the test results. In some embodiments, one or more persons associated with a health care provider can customize test results reports. For example, a health care provider may have a customized test results report template and a doctor employed by the health care provider may have another customized test results report template. Thus, various entities or people associated with various entities, or both, may be able to customize test reports. In some embodiments, a patient may be able to customize test results reports. Variations are within the scope of this disclosure and will be apparent to one of skill in the art.

The description above with reference to illustrative examples is provided to introduce the reader to the general subject matter discussed herein. The invention is not limited to the illustrative examples. The following sections describe various additional non-limiting embodiments and examples of devices, systems, and methods for laboratory testing management.

Physician Decision Support Component

A non-limiting example of a physician decision support component of a laboratory benefit management system according to an embodiment of the present invention is set forth below. For example, one or more steps described with respect to decision support may be performed in the processing component discussed above. The description will be made with respect to FIG. 1, which illustrates an example environment 100 for implementing aspects in accordance with various embodiments.

Physician decision support (PDS) is a feature of an embodiment of a system and/or a method of the present invention. In an embodiment, physician decision support assists a health care provider in selecting a laboratory test, or tests, for a patient based on current medical guidelines and may also facilitate test ordering. In an embodiment, at the point-of-order and care, a system and/or method of the present invention will enable a health care provider to select a laboratory that is qualified to perform the selected tests according to published criteria. As will be appreciated by those of ordinary skill in the art, such tools assist health care providers in optimizing the choice of test for their patients and in selecting a laboratory with expertise to perform the selected tests.

The physician decision support may begin with processing of patient information. The processing may comprise analyzing patient information and applying a policy and/or policies to provide options for laboratory tests. The options for laboratory tests may be further processed with reference to laboratory information, and/or health plan information. The laboratory test options and/or the laboratory options may be presented to a health care provider. In certain embodiments, the laboratory test options and/or laboratory options may be integrated with an ordering system of a laboratory, by way of non-limiting example, the system described in commonly assigned, co-pending, U.S. patent application Ser. No. 13/723,384, filed Dec. 21, 2012, entitled Systems, Methods, and Media for Laboratory Testing Services, the disclosure of which is hereby incorporated herein by reference.

The processing of laboratory information may comprise verification of a test. A test verification may be based on one or more medical classification lists. For example, a laboratory test requested for a patient may be verified against an ICD-9 or ICD-10 medical classification list. In an embodiment, the request contains a code that represents a laboratory test to be performed for a patient. The code specified in the request may be compared with codes provided in ICD-10 to determine whether the code is a valid code. In one embodiment, if the code specified in the request is also listed in the ICD-10 list, then a determination may be made that the code is valid. Otherwise, in this embodiment, the code specified in the request may be determined to be invalid. A request may contain a name of a laboratory test to be performed. In this embodiment, a code—such as an ICD-9, ICD-10, or CPT code—may be assigned for the laboratory test based at least in part on the name of the laboratory test. For example, if the name of the laboratory test provided in the request matches a name of a laboratory test listed in an ICD-10 classification list, then the ICD-10 number associated with that laboratory test may be assigned.

In one embodiment, a classification code for a laboratory test may be assigned that closely matches the name of a laboratory test provided in a request. In some embodiments, if a code cannot be ascertained for one or more laboratory tests specified in a request, then information is sent to the requestor asking for more information. For example, if a request is received by server 190 from tablet computer 130 for a laboratory test and server 190 cannot determine a classification code for the laboratory test, then server 190 may send a response to the tablet computer 130 requesting additional information for the laboratory test. As an example, the server 190 may request that a classification code for the laboratory test be provided. As another example, the server 190 may request that a revised name for the laboratory test be submitted. In one embodiment, the server 190 may provide the tablet computer 130 with a list of potential laboratory names and the user of the tablet computer 130 can select the appropriate laboratory name. Once additional information has be input into the tablet computer 130, then an updated response may be sent from the tablet computer 130 to server 190 through network 105.

In performing a test verification for at least a portion of a request, information may be requested from one or more data stores in one or more locations. In one embodiment, server 190 accesses information stored in data store 195 in performing a test verification for at least a portion of an order. For example, data store 195 may contain a list of ICD-10 codes. In this embodiment, a laboratory test specified in a request received by server 190 may be compared to the list of ICD-10 codes in data store 195 to verify that the laboratory test specified in the request is valid. In another embodiment, server 190 accesses information stored in one or more external data stores to perform a test verification for at least a portion of an order. For example, referring to FIG. 2, a data store related to a health plan provider 285 may contain a classification list of various laboratory tests. In this embodiment, server 190 may access information stored in data store 285 to perform a test verification.

Processing of patient information in view of a policy may result in the selection of one or more laboratory tests for presentation to a health care provider. A determination as to whether one or more laboratory tests are presented to a health care provider may be made in any number of ways. In one embodiment, a determination as to whether one or more laboratory tests are available may be based on a policy comprising evidence based guidelines. Evidence based guidelines may be derived from any number of medical sources including, but not limited to, journals, articles, case studies, publications, various data stores containing medical information, or other medical literature. In some embodiments, evidence based guidelines can be based on clinical trials, risk-benefit analyses, medical literature, meta-analysis, or a combination thereof. Evidence based guidelines may be based on one or more symptoms, illnesses, policies, or a combination thereof. In one embodiment, evidence based guidelines may be tailored to one or more patients based at least in part on a patient's current symptoms or medical history, or both. As will be realized by those of ordinary skill in the art, there may exist situations where a health care provider provides information relating to a test that he/she thinks is appropriate based on patient information. In an embodiment, the health care provider's test may be presented together with one or more alternative laboratories tests based on processing such as that described herein.

In one embodiment, a data store 195 containing a policy comprising evidence based guidelines is accessed to determine whether one or more tests are recommended. For example, a request received by server 190 may contain an illness or a disease for a patient, such as high cholesterol. In this embodiment, server 190 accesses data store 195 to determine if there are any policies relating to tests that are recommended based on the illness or disease provided in the request for the patient and the evidence based guidelines stored in data store 195. In one embodiment, historical medical information for the patient is also used to determine which tests, if any, are recommended. As another example, a request received by server 190 may contain a laboratory test for a patient. In this embodiment, server 190 may access policies comprising evidence based guidelines stored in data store 190 to determine whether one or more additional or alternative tests associated with the requested laboratory test is recommended based at least in part on the evidence based guidelines.

In an embodiment, a determination as to whether present one or more laboratory tests may be made on patient information, comprising current symptoms of a patient. For example, patient information received by server 190 may comprise a list of current and/or past symptoms for a patient. In an embodiment, server 190 accesses data store 195 comprising a policy or policies to determine if there are any tests that are recommended based on the symptoms. In one embodiment, patient information comprising historical medical information for the patient is also used to determine which tests, if any, are recommended. For example, if a patient has a history of having a bladder infection and symptoms for the patient provided in the patient information suggest a bladder infection, among other potential illnesses, then one or more laboratory tests related to a bladder infection may be presented. In an embodiment, patient information comprises laboratory test data. In this embodiment, server 190 may access a policy or policies stored in data store 195 to determine whether one or more additional tests are presented based at least in part on the requested laboratory test as well as the patient's symptoms. The foregoing are illustrative examples of the use of patient information to present laboratory tests. As discussed herein, patient information may comprise current symptoms, medical history, past symptoms, laboratory test performed and the results and a variety of other information set forth above. As will be understood from the preceding discussion, a determination as to whether to present one or more laboratory tests to a health care provider may be made based on at least one datum or set of data included within patient information and/or a plurality of data included with patient information.

As noted herein, in various embodiments, a policy, e.g. a policy comprising evidenced based guidelines; symptoms, historical medical information, illnesses or diseases, any laboratory tests, or a combination thereof, may be used to determine one or more tests to present to a health care provider or other user of the system. One or more data stores may be queried in making such a determination. In one embodiment, information is contained in a single data store. For example, in FIG. 1, data store 195 may contain historical medical information for a patient and evidence based guidelines that are used, along with information received in the request, to determine whether one or more tests are recommended. In another embodiment, information is contained in two or more data stores. For example, referring to FIG. 2, data store 205 may contain medical codes, data store 280 may contain evidence based guidelines for the health care provider, and data store 285 may contain historical information for patients. In this embodiment, server 190 may receive a request for a laboratory test and a list of symptoms for a patient. In determining whether one or more tests are recommended, server 190 may access data store 205 for one or more medical codes related to the requested laboratory test, data store 280 for evidence based guidelines based on the list of symptoms for the patient provided in the request or the requested laboratory test, or both, and data store 285 for historical information related to the patient.

In embodiments, information presented relating to a laboratory test may include, but is not limited to, one or more classification codes for the laboratory test, a name for the laboratory test, one or more reasons as to why the laboratory test is recommended, medical information related to the recommended laboratory test and a patient for which the laboratory test is recommended, statistics related to the laboratory test, information regarding evidence based guidelines that were used to make the recommendation, one or more medical references regarding the recommendation, other medical information, or a combination thereof. In embodiments, information presented may be customized. For example, a health care provider may specify that a list of tests and/or laboratories should be presented. A physician in doctor's office 110, however, may specify that a list of laboratory tests as well as the criteria, for example the policy, used to determine the laboratory tests should be provided. In another embodiment, a physician can specify that a laboratory test as well as any relevant medical articles should be presented. Thus, in various embodiments, customized recommendations may be provided to users based on customization settings of the user or an organization associated with the user. For example, a hospital 120 may determine a level of customization for recommended tests. In one embodiment, a user of the laboratory benefits management system, such as a health care provider, can determine a level of customization for recommended tests.

The presentation of information to a user of the system, or in a method of the present invention, may be accomplished in any number of ways. In an embodiment, information may be presented on a web page, accessible through a web portal. For example, if a physician is using desktop computer 115 to access a web portal, then the server 190 may send information related to the available tests to desktop computer 115 through network 105. In another embodiment, tablet computer 130 is executing software, such as a touchscreen-enabled application, that presents information to a user of the tablet computer 130. In one embodiment, tablet computer 130 may contain sufficient information on the device to make a determination as to whether additional tests are available and to present additional tests to a user. Such information may be stored on memory in the tablet computer, on a disk drive in the tablet computer, or one or more external storage devices. In another embodiment, tablet computer 130 may send and receive information from other devices, such as server 190.

Health plan information may be utilized to present patient benefit information relating to one or more laboratory tests, and/or with respect to one or more laboratories.

Health plan benefit information, laboratory information and/or laboratory test information may be processed and/or presented in any number of ways. In one embodiment, information is transmitted over hypertext transfer protocol (HTTP). Information may be received via a secure connection. For example, information may be received over hypertext transfer protocol secure (HTTPS). In one embodiment, information is received over a virtual private network (VPN) connection. Information may be received through one or more application programming interfaces (APIs). In an embodiment, information is received from a website associated with a laboratory benefits organization, a health care provider, or a third-party. Information may be transmitted and exchanged in any number of languages or in any number of formats including, but not limited to, ActionScript®, AJAX, ASP, C, C++, HTML, JAVA JavaScript, JSON, JSP, MXML, PHP, XML, or XSLT. In embodiments, information may be received from one or more data stores. For example, information may be received from a data store associated with a health care provider. Information may be in an archive or compressed format, or both, such as JAR, ZIP, RAR, ISO, or TAR. A combination of protocols, languages, formats, and/or devices may be used to send or receive a response according to various embodiments.

In an embodiment, patient eligibility for a laboratory test may be verified using health plan information for the patient. Patient eligibility may be determined in any number of ways. In one embodiment, patient eligibility is verified using information contained in one or more data stores. In another embodiment, server 190 may query one or more external data stores, such as health plan provider data store 285 shown in FIG. 2, to make a determination as to whether a patient 145 is eligible.

Numerous factors may be used to determine whether a patient is eligible for one or more laboratory tests. In one embodiment, health plan membership data may be used to determine whether a patient is eligible for the one or more laboratory tests. For example, server 190 may query data store 195 to determine whether a patient associated with the one or more laboratory tests is currently an active member in a health plan for a health plan provider. If a determination is made that the patient is an active member in the health plan, then the patient may be determined to be eligible for the one or more laboratory tests. If a determination is made that the patient is not currently an active member in the health plan, then the patient may be determined to be ineligible for the one or more laboratory tests. As another example, a determination may be made as to whether a patient for which a particular laboratory test is ordered has waited a required period of time since receiving the particular laboratory test or a related laboratory test, or both. If a determination is made that the patient has not waited the required period of time, then an alternative laboratory test for which the period of time is not required may be recommended. In one embodiment, the decision support component asks a health care provider ordering a laboratory test for a patient a series of questions to determine whether the patient is currently eligible to receive the laboratory test under the patient's health plan provider. Numerous other examples are disclosed herein and variations are within the scope of this disclosure.

As noted above, patient benefits related to the one or more laboratory tests may be presented to a health care provider and/or another user of the system. For example, a maximum payment for the one or more laboratory tests based on health plan information may be presented. A maximum payment may be based on any number of factors. A maximum payment may be based on the type of laboratory test that will be performed. A maximum payment can be based on a volume or number of laboratory tests performed within a timeframe. In one embodiment, a maximum payment may be based on a turnaround time. For example, a laboratory test that needs completion within two days may have a higher maximum payment than the same laboratory test that needs completion within one week. In embodiments, a maximum payment may be based on a health plan provider associated with a patient for whom a laboratory test will be performed. For example, a health plan provider may allow a maximum payment for a particular laboratory test. In this embodiment, the maximum payment to an internal or external laboratory may be based at least in part on the maximum payment allowed by the health plan provider.

In determining patient benefits for the one or more laboratory tests, information stored in one or more data stores may be accessed. For example, referring to FIG. 1, server 190 may access information stored in data store 195. In some embodiments, information from one or more external sources may be used to determine patient benefits for the one or more laboratory tests. For example, server 190 may send a request to desktop computer 165 associated with health plan provider 160. In this embodiment, the request may be for a maximum reimbursement amount for a laboratory test associated with a patient having a particular plan. In response to the request, server 190 may receive a response from desktop computer 165. In another embodiment, numerous data stores may be queried to determine benefits. For example, referring to FIG. 2, information stored in laboratory management data store 205, health plan provider data store 285, and laboratory data store 290 may each be queried to determine patient benefits for one or more laboratory tests. For example, laboratory data store 290 may be queried to determine a testing identification number for a laboratory test associated with an order. In this embodiment, information stored in database 245 may be queried to determine a patient associated with the testing identification number. In addition, patient database 215 may be queried to determine a health plan provider and policy number associated with the patient. Furthermore, health plan data store 285 may be accessed to determine a maximum reimbursement price for the laboratory test.

After information is presented to a health care provider, the provider may select one or more tests to be run. In an embodiment, after selection a notification may be provided to one or more users of the laboratory management system. For example, if a nurse originally submits an order for a physician, then the nurse or the physician, or both, may receive a notification that the order has been approved. In embodiments where a request contains tests for multiple patients associated with multiple physicians, then each physician may receive a notification associated with his or her patients. For example, a request may contain a laboratory test request for patient A associated with physician A, a laboratory test request for patient B associated with physician A, and a laboratory test request for patient C associated with physician B. In this embodiment, physician A may receive one notification for the laboratory test request associated with patient A and another notification for the laboratory test request associated with patient B. Alternatively, physician A may receive a single, combined notification for the laboratory test requests associated with patient A and patient B. In addition, physician B may receive a notification for the laboratory test request associated with patient C.

In embodiments, one or more patients may receive a notification related to an order. For example, patient A may receive a notification that a laboratory test has been ordered and approved. A patient may receive information indicating additional steps that the patient needs to complete in order for the order to be finished. In one embodiment, the notification may provide information needed to obtain a sample from the patient. For example, a patient may need to have blood drawn in order to complete a laboratory test. In this embodiment, the notification to the patient may provide a date, time, and location for the patient to have the blood drawn. A notification may contain additional instructions for a patient. For example, a patient may need to fast for twelve hours before an appointment. In this embodiment, the notification may state that the patient should not eat within twelve hours of the appointment. Numerous other embodiments will be obvious to one of skill in the art.

As will be appreciated from the discussion herein, embodiments of the present invention may be advantageously used in a health care environment to connect health care providers, payers and diagnostic test providers to deliver high quality, cost effective care to an individual seeking health care services.

As discussed herein a feature of the present invention comprises decision support. Embodiments of systems, components and methods of the present invention may provide decision support to assist a user in decision making Decision support may comprise receiving input and providing a suggested course of action based on the input and data. Input may comprise patent data. Patient data may comprise: identification data, electronic medical record (EMR) data, physical specifications (height, weight, age), medical history, insurance coverage information, family history and the like. Data may comprise data relating to: a patient, a laboratory, clinical outcomes in similar cases, clinical research, specific tests and the like.

In an embodiment, decision support may comprise a guideline, including but not limited to a guideline relating to: diagnostic test selection, interpretation of test results, follow on testing, additional tests, laboratory selection, identification of appropriate patients for testing, explanation of test results, insurance coverage and insurance coding. A guideline may comprise background data. A guideline may also be sometimes referred to herein as a policy. An embodiment of the present invention may comprise a guideline or policy, or a plurality of guidelines or policies.

As will be understood by those of skill in the art, background data is often temporal and may be updated to reflect changes in a patient, laboratory, clinical outcomes, clinical research, specific tests and/or other datum. A guideline or policy in an embodiment of the present invention may also be temporal and subject to updating and/or changes in view of altered background data.

By way of a non-limiting example, a policy may relate to a diagnostic test, including a diagnostic test for a particular condition or disease. Examples of diagnostic tests include, but are not limited to: urinary tract infections; human immunodeficiency virus (HIV) testing, prognosis, monitoring and/or diagnosis; blood counts; partial thromboplastin time; prothrombin time; serum iron studies; collagen cross-links; blood glucose testing; glycated hemoglobin/glycated protein; thyroid testing; lipid testing; digoxin therapeutic drug assay; alpha fetoprotein; carcinoembryonic antigen (CEA); human chorionic gonadotropin (HCG); tumor antigen by immunoassay (including, but not limited to, CA 125; CA 15-3/CA 27.29; CA 19-9; prostate specific antigen; gamma glutamyl transferase (GGT); hepatitis panel/acute hepatitis panel; fecal occult blood test; as well as all of the tests found at https://www.labcorp.com/wps/portal/testmenu and/or the tests offered by other clinical diagnostic laboratories now or in the future.

Policies may also relate to conditions or diseases. Examples of conditions and/or diseases include, but are not limited to, allergies (food, insect, mold, dust, animal, chemicals and the like); diarrhea; celiac disease; lyme disease; diabetes; arthritis; thalassemia; viral infections; bacterial infections; cold; flu; upper respiratory tract infections; urinary tract infections; gastroenterological conditions; urological conditions; cardiovascular conditions; cancers, including but not limited to: lung, ovarian, prostrate, skin, lymphatic, colon, liver, brain, leukemia and other metastatic and non-metastatic cancers, as well as all of the cancers listed by the National Cancer Institute, see, e.g. http://www.cancer.gov/cancertopics/types/alphalist; as well as all of the conditions found at https://www.labcorp.com/wps/portal/provider/testmenu and/or referenced by other clinical diagnostic laboratories now or in the future.

Policies may also relate to particular health care specialties including, but not limited to, allergy; immunology; cardiology; dermatology; endocrinology; gastroenterology; infectious disease; internal medicine; nephrology; neurology; obstetrics; gynecology; pathology; pediatrics; primary care; psychiatry; rheumatology; urology; routine testing; as well as other existing and/or to be developed specialties.

As described herein decision support may comprise a policy relating to a diagnostic test; condition, disease and/or specialty. In an embodiment a policy comprises data relating to one or more of a diagnostic test; a condition; a disease; and/or specialty. By way of a non-limiting example, decision support may comprise associating a patient datum or patient data with data relating to one or more of a diagnostic test; a condition; a disease; and/or specialty.

Laboratory Presentation Component

As noted herein, the information presented in an embodiment of a system or method of the present invention may comprise information relating to laboratory where a test may be performed. The selection of laboratories to be presented may be made based on laboratory information from one or more laboratories. In one embodiment, one or more labs are presented based on the test or tests to be presented. For example, a first test and a second test may be presented for a patient. In this embodiment, a first laboratory may perform the first test, a second laboratory may perform the second test, and a third laboratory may perform both the first and the second test. In this embodiment, information may be presented and a decision may be made by a health care provider that the third laboratory should complete the first and second laboratory tests for this order because the third laboratory can perform both tests. In another embodiment, a the health care provider may determine that the first laboratory should complete the first laboratory test and that the third laboratory should complete the second laboratory test because of one or more other factors disclosed herein, including, but not limited to, laboratory qualifications, test processing time, health plan benefit information and the like. Furthermore, the second laboratory may not be chosen to complete the first laboratory test because the second laboratory does not perform the first laboratory test.

In one embodiment, one or more labs are determined based on processing time. For example, two labs may perform a laboratory test ordered for a patient. In this embodiment, however, processing pursuant to a policy may present information that test results received in one week are desirable. The processing time of one laboratory may allow test results to be received in one week whereas the processing time of another laboratory suggests that test results will not be received in one week. In an embodiment, the information presented may comprise processing times. In a similar fashion, the location of a laboratory may be presented to enable a health care provider to select a laboratory testing facility closer to the health care provider.

In another embodiment, multiple laboratories may be presented for a single test. For example, one laboratory facility—such as a physician office laboratory—that is in close proximity to a patient may be presented for collecting a sample from the patient for the laboratory test while another laboratory facility may be presented for sample analysis.

In one embodiment, health plan information may be utilized to present one or more labs based on whether the labs are in network or out of network. For example, if two labs are available to perform a laboratory test for an order and one laboratory is an in-network laboratory and the other laboratory is an out-of-network laboratory, then the in-network laboratory may be presented in a way to distinguish it from the out-of-network laboratory.

In embodiments, presentation and selection of one or more laboratory may be based on a combination of factors. Selection of a testing facility by a health care provider and/or a patient may also be based on a number of factors, services offered, availability, location, cost, whether the laboratory is an in-network or out-of-network laboratory, or a combination thereof. In an embodiment, health care provider and/or patient laboratory selection criteria comprises at least part of the information presented.

In embodiments, one or more laboratory testing facilities may be presented based at least in part on statistical information related to one or more testing facilities. For example, one or more laboratories may be presented based on the accuracy, reliability, or other statistics associated with a laboratory.

An embodiment of a system or method of the present invention may include a notification component for sending notifications to a user of the system, or performer of the method. The notification may comprise information relating to a laboratory test, including status, sample location, processing unit, and/or results, or availability of results. A notification may be sent in any form including, but not limited to, a text message, an email, a fax, an automated phone call, or other electronic notifications. In one embodiment, a laboratory testing facility may be able to access one or more web pages associated with the laboratory benefits organization that provides notification of orders. Information regarding orders may be stored in a data store, such as data store 195 shown in FIG. 1. For example, data store 195 may contain a list of completed orders as well as a list of pending orders that need to be completed.

In embodiments, one or more notifications may be provided that indicate that test result information is available. For example, a notification may be sent to a health care provider or a physician, or both, and the notification may indicate that one or more test results for a patient associated with the health care provider or physician are available. A notification may be provided to a patient associated with the laboratory test. In one embodiment, a test results report may automatically be sent to a health care provider, physician, patient, or a combination thereof when test results are saved. As discussed herein, test results reports may be customized. Thus, customized test results reports may be sent to various parties. A notification or test results, or both, may be sent in numerous ways. For example, a notification or test results may be sent via email, SMS, or an automated telephone call. A notification may be provided in response to a received request. For example, server 190 may receive a request for one or more outstanding notifications. In this embodiment, server 190 may query data store 195 to determine whether there are any outstanding notifications. If one or more notifications are outstanding, then sever 190 may send at least a portion of the notifications to a device that requested the notifications. A notification may be provided to a website or an application being executed on a user device. Variations are within the scope of this disclosure.

Test results reports may be generated in any number of ways. In one embodiment, the results of one or more tests is provided in response to a request from a device in communication with the laboratory benefits organization. For example, tablet computer 130 may send a request to server 190 through network 105 and network 125 that indicates that a user of the tablet computer 130 wants to view the results of one or more tests. In this embodiment, server 190 receives the request. Server 190 may query data store 195 for the requested test results or other medical information needed to customize the test results report. In one embodiment, data store 195 contains a document—such as an HTML file, a DOC file, a DOCX file, or a PDF file—that the server 190 can send to the tablet computer 130. In other embodiments, data store 195 contains test results data or other medical information, such as information used to customize a test results request. In this embodiment, server 190 queries data store 195 and uses at least some of the information received from data store 195 to generate a customized test results report. The server 190 can send the customized test results report to the table computer 130. A test results report may be sent in any number of formats including, but not limited to, numerical data, plain text, HTML, XML, DOC, DOCX, PDF, XLS, etc. In one embodiment, test results information may be stored in a proprietary format. In another embodiment, information related to one or more test results is sent to one or more applications being executed on a user device. For example, server 190 may send one or more test results reports to an application on desktop computer 115.

Test results reports may be provided at various times to one or more users of the laboratory management system once test results have been saved. Tests results may automatically be sent to one or more users. For example, a doctor associated with hospital 120 may receive test results for one or more laboratory tests as soon as the results become available. Another physician associated with doctor's office 110 may receive test results on a periodic basis such as once per hour, once per day, every Monday, every four hours, or some other periodic timeframe. Various entities and users may be able to customize the delivery of tests results reports so that they receive reports at times specified by the entity or user.

A test results report can contain information for the current laboratory test as well as information for various demographics. For example, a test results report may compare the current test results with test results for an overall population. A test results report may compare the current test results with test results from other patients having one or more similar circumstances including, but not limited to, the same age range, the same gender, the same weight, the same height, one or more common symptoms, one or more common illnesses, one or more common other laboratory tests, other medical information, or a combination there. Thus, a test results report may compare a patient's current laboratory tests results with various statistical information associated with other laboratory tests.

In embodiments, a test results report may contain one or more additional recommended tests based on analysis of the patient information including the test result in view of a policy or policies. For example, based at least in part on the results of the current laboratory test, a determination may be made that one or more additional laboratory tests should be performed. A determination that one or more additional tests are recommended can be based on various sources of medical information. In one embodiment, a determination is made based at least in part on the results of other laboratory tests, such as the results of the same type of laboratory tests that were conducted on other samples or other related laboratory tests. In another embodiment, a determination is made based at least in part on medical history for the patient. One or more tests may be recommended based on evidence based guidelines. In some embodiments, one or more additional tests may be recommended based on other medical literature.

In embodiments, a test results report can contain additional information such as suggestions for follow on/recurring testing, health guidelines relating to a disease or condition, advertisements, and the like. In embodiments, a test results report may contain one or more potential courses of action. For example, a potential course of action may be determined based at least in part on the results of the current laboratory test. A potential course of action may be determined based on various sources of medical information. In one embodiment, a potential course of action may be determined based at least in part on the results of other laboratory tests, such as the results of the same type of laboratory tests that were conducted on other samples or other related laboratory tests. In another embodiment, a potential course of action may be determined based at least in part on the medical history of the patient, such as previous test results for the patient. One or more potential courses of action may be based on evidence based guidelines. In some embodiments, one or more potential courses of action may be based on medical literature.

One or more entities or users may be able to customize the information contained in one or more test results report. For example, a physician may be able to customize test results reports so that only raw test results data is provided in a test results report. In another embodiment, a user can customize test results reports to include historical medical information related to a patient for which a laboratory test was performed. For example, a tests results report may contain results of the current laboratory test as well as the results of previous laboratory tests for the patient. In one embodiment, current test results or historical tests results, or both, may be provided in a graphical format. For example, one or more bar charts or line charts may be included in a test results report that graphically demonstrate information related to the laboratory test. In some embodiments, one or more test results reports may be customized to include demographic information, additional recommended tests, potential diagnostic information, potential courses of action, other medical information, or a combination.

In embodiments, one or more entities or users may be able to control the level of customization. For example, referring to FIG. 1, hospital 120 may determine that physicians associated with the hospital can choose whether or not a test results report includes additional recommended tests or potential diagnostic information, but that physicians cannot receive test results reports that contain potential courses of action. In this embodiment, one physician associated with the hospital 120 can choose to receive a test results report that includes both additional recommended tests and potential diagnostic information. Another physician associated with hospital 120 may choose to receive test result reports that include additional recommended tests. In this embodiment, however, neither physician associated with hospital 120 can receive a test results report that includes potential courses of action because hospital 120 has disabled this option. In other embodiments, hospital 120 may let each physician associated with hospital 120 customize a test results report in any available manner. Thus, in embodiments, a level of allowable customization is based on a hierarchy of entities or users, or both.

In an embodiment, a patient for which a laboratory test was conducted can receive the results of the laboratory test. In one embodiment, the patient can customize the test results report as disclosed herein. In other embodiments, a health care provider may determine the information that a patient receives in a test result report. The patient may receive the same test results report as a physician associated with the patient. Alternatively, a physician may receive one test results report for a laboratory test and the patient for which the laboratory test was performed may receive a different test results report. For example, the physician's test results report may contain one or more potential diagnoses as well as one or more recommended courses of action and the patient's test results report may contain the results of the laboratory test as well as the test results of other laboratory tests that were previously performed for the patient.

General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Such computing devices may include, but are not limited to, desktop computers, mobile phones, personal digital assistants (PDAs), tablet computers, laptops, smartphones, Wi-Fi enabled computing devices, 3G or 4G enabled computing devices, or other suitable computing devices. Suitable computing devices include multipurpose microprocessor-based computer systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel. Thus, while the steps of methods disclosed herein have been shown and described in a particular order, other embodiments may comprise the same, additional, or fewer steps. Some embodiments may perform the steps in a different order or in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

The use of "an embodiment", "one embodiment", "embodiments" and similar references is meant as open an inclusive language that not does limit the embodiment from including additional components, steps, features, task or the like described with respect to other embodiments. A system or method of the present invention may comprise one, or a plurality of the embodiments described herein.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

That which is claimed is:

1. A method, comprising:
generating, by a pass through server, a web portal in a number of portal pages presented by use of portlets, the web portal provideable to an electronic device of a health care provider and useable for receiving user input via the electronic device;
receiving, by the pass through server and from the electronic device of the health care provider, an order request for a first laboratory test for a patient corresponding to the health care provider via the web portal;
verifying, by the pass through server and in response to receiving the order request and prior to completing an order corresponding to the order request for the first laboratory test, an authenticity of the health care provider by authenticating a username and password or a digital certificate associated with the health care provider, wherein verifying the authenticity of the health care provider comprises:
    accessing, by the pass through server, an authenticity data store to determine whether the username and password or the digital certificate received from the electronic device of the health care provider authenticates the health care provider;
    in response to verifying the authenticity of the health care provider and after receiving the order request for the first laboratory test and prior to completing the order corresponding to the order request for the first laboratory test:
dynamically determining, by an application server in a clustered server environment, a recommended laboratory test for the patient based at least in part on the first laboratory test for the patient and by querying a data store in communication with the application server for medical information corresponding to the patient stored in the data store;
wherein the medical information stored in the data store used in dynamically determining the recommended laboratory test for the patient comprises a medical classification code corresponding to the patient, a health plan corresponding to the patient, and historical medical information corresponding to the patient;
wherein the recommended laboratory test comprises at least one of an additional laboratory test for the patient or an alternate laboratory test for the patient;
determining an availability of a previous sample from the patient for the recommended laboratory test, wherein the availability includes an existence of and a duration of the existence of the previous sample;
sending, by the pass through server and via the web portal, the recommended laboratory test for the patient and an alert based on the availability of the previous sample for the recommended laboratory test to the electronic device of the health care provider asking whether the recommended laboratory test for the patient should be ordered;
receiving, by the pass through server and via the web portal, a response from the electronic device of the health care provider to order the recommended laboratory test for the patient;
completing the order from the health care provider based at least in part on the determining of the availability, wherein the order comprises the recommended laboratory test for the patient;
receiving, by the pass through server and via the web portal, a plurality of selections made on the electronic device of the health care provider to define a presentation customization, the plurality of selections including a selection for displaying raw data, a selection for displaying historical medical information, and a selection for displaying graphical indications;
dynamically generating a test result report in accordance with the presentation customization; and
electronically sending the test result report to at least one of the patient or the health care provider.

2. The method of claim 1, wherein the order further comprises the first laboratory test.

3. The method of claim 2, wherein the order request further comprises a first laboratory facility to perform the first laboratory test, and wherein the method further comprises:

after receiving the order request and prior to completing the order corresponding to the order request for the first laboratory test:

dynamically determining, by the application server, an alternate laboratory facility to perform the first laboratory test and the recommended laboratory test, wherein the alternate laboratory facility is determined based at least in part on the first laboratory test, the recommended laboratory test, and the health plan for the patient; and wherein the order comprises the alternative laboratory facility to perform both the first laboratory test and the recommended laboratory test.

4. The method of claim 1, wherein the medical classification code comprises at least one of an International Statistical Classification of Diseases and Related Health Problems (ICD) code or an American Medical Association (AMA) CPT code.

5. The method of claim 1, wherein the recommended laboratory test comprises the alternate laboratory test to the first laboratory test, and wherein the order does not comprise the first laboratory test.

6. The method of claim 5, wherein the alternate laboratory test is determined based at least in part on a potential illness corresponding to a current symptom of the patient, and wherein the alternate laboratory test is configured to diagnose the potential illness.

7. The method of claim 6, wherein the alternate laboratory test is further determined based at least in part on an evidence-based guideline.

8. The method of claim 7, wherein the evidence-based guideline is based on a medical journal article, a medical case study, or a clinical trial.

9. The method of claim 5, wherein the alternate laboratory test is determined based at least in part on a determination that the alternate laboratory test is a prerequisite to the first laboratory test and that the patient has not received the first laboratory test.

10. The method of claim 5, wherein the alternate laboratory test is determined based at least in part on a first determination that a predetermined time period required before the patient is eligible for the first laboratory test has not passed and a second determination that the patient is eligible for the alternate laboratory test.

11. The method of claim 5, wherein the alternate laboratory test is determined based at least in part on a maximum reimbursement amount corresponding to the alternate laboratory test.

12. The method of claim 5, further comprising: dynamically determining a laboratory facility to perform the alternate laboratory test.

13. The method of claim 12, wherein the order request comprises a first laboratory facility to perform the first laboratory test, and wherein the determined laboratory facility is a same laboratory as the first laboratory facility.

14. The method of claim 12, wherein the laboratory facility is determined based at least in part on a maximum reimbursement amount for the alternate laboratory test when performed at the laboratory facility.

15. The method of claim 12, wherein the medical information comprises the health plan for the patient and wherein the laboratory facility is determined based at least in part on the health plan for the patient, an expertise of the laboratory facility in performing the alternate laboratory test, a cost of performing the alternate laboratory test at the laboratory facility, and a capacity of the laboratory facility to perform the alternate laboratory test within a predetermined turnaround time.

16. The method of claim 1, wherein the test result report is formatted based at least in part on a predefined preference of the patient.

17. The method of claim 1, wherein the test result report is sent to the health care provider based on a predetermined delivery preference of the health care provider.

18. The method of claim 1, further comprising:
determining a recommendation for the patient to have a follow-up laboratory test, wherein the recommendation is determined based at least in part on a test result, wherein the test result report comprises the recommendation.

19. The method of claim 18, wherein the recommendation is further determined based at least in part on the historical medical information and an evidence-based guideline corresponding to the test result and the follow-up laboratory test.

20. The method of claim 1, wherein the test result report comprises a chart corresponding to test results of a population of patients that previously received the recommended laboratory test.

21. The method of claim 1, wherein the test result report comprises a chart of a historical medical indicator of the patient, the historical medical indicator corresponding to the recommended laboratory test.

22. A system, comprising:
an electronic device of a health care provider;
an application server in a clustered server environment;
a pass through server; and
a data store in communication with the pass through server and the application server, wherein the pass through server is configured to:
generate a web portal in a number of portal pages presented by use of portlets, the web portal provideable to the electronic device of the health care provider and useable for receiving user input via the electronic device;
receive, from the electronic device of the health care provider, an order request for a first laboratory test for a patient corresponding to the health care provider via the web portal;
verify, in response to receiving the order request and prior to completing an order corresponding to the order request for the first laboratory test, an authenticity of the health care provider by authenticating a username and password or a digital certificate associated with the health care provider, wherein verifying the authenticity of the health care provider comprises:
accessing an authenticity data store to determine whether the username and password or the digital certificate received from the electronic device of the health care provider authenticates the health care provider;
in response to verifying the authenticity of the health care provider and after receiving the order request for the first laboratory test and prior to completing an order corresponding to the order request for the first laboratory test:
dynamically determine, by the application server, a recommended laboratory test for the patient based at least in part on the first laboratory test for the patient and by querying the data store in communication with the application server for medical information corresponding to the patient stored in the data store;
wherein the medical information stored in the data store used in dynamically determining the recommended laboratory test for the patient comprises a medical classification code corresponding to the patient, a health plan corresponding to the patient, and historical medical information corresponding to the patient;
wherein the recommended laboratory test comprises at least one of an additional laboratory test for the patient or an alternate laboratory test for the patient;
determine an availability of a previous sample from the patient for the recommended laboratory test, wherein the availability includes an existence of and a duration of the existence of the previous sample;
send the recommended laboratory test for the patient and an alert based on the availability of the previous sample for the recommended laboratory test to the electronic device of the health care provider asking whether the recommended laboratory test for the patient should be ordered;
complete the order from the health care provider based at least in part on the determining of the availability, wherein the order comprises the recommended laboratory test for the patient;
receiving, by the pass through server and via the web portal, a plurality of selections made on the electronic device of the health care provider to define a presentation customization, the plurality of selections including a selection for displaying raw data, a selection for displaying historical medical information, and a selection for displaying graphical indications;
dynamically generate a test result report in accordance with the presentation customization; and
electronically send the test result report to at least one of the patient or the health care provider.

23. A non-transitory computer-readable medium comprising one or more software applications configured to be executed by a processor, the one or more software applications configured to:
generate a web portal by a pass through server in a number of portal pages presented by use of portlets, the web portal provideable to an electronic device of a health care provider and useable for receiving user input via the electronic device;
receive, from the electronic device of the health care provider, an order request for a first laboratory test for a patient corresponding to the health care provider via the web portal;
verify, in response to receiving the order request and prior to completing an order corresponding to the order request for the first laboratory test, an authenticity of the health care provider by authenticating a username and password or a digital certificate associated with the health care provider, wherein verifying the authenticity of the health care provider comprises:
accessing, by the pass through server, an authenticity data store to determine whether the username and password or the digital certificate received from the electronic device of the health care provider authenticates the health care provider;
after receiving the order request for the first laboratory test and prior to completing an order corresponding to the order request for the first laboratory test:
dynamically determine, using an application server in a clustered server environment, a recommended laboratory test for the patient based at least in part on the first laboratory test for the patient and by querying a data store for medical information corresponding to the patient stored in the data store;
wherein the medical information stored in the data store used in dynamically determining the recommended laboratory test for the patient comprises a medical classification code corresponding to the patient, a health plan corresponding to the patient, and historical medical information corresponding to the patient;
wherein the recommended laboratory test comprises at least one of an additional laboratory test for the patient or an alternate laboratory test for the patient;
determine an availability of a previous sample from the patient for the recommended laboratory test, wherein the availability includes an existence of and a duration of the existence of the previous sample;
send the recommended laboratory test for the patient and an alert based on the availability of the previous sample for the recommended laboratory test to the electronic device of the health care provider asking whether the recommended laboratory test for the patient should be ordered;
receive a response from the electronic device of the health care provider to order the recommended laboratory test for the patient;
complete the order from the health care provider based at least in part on the determining of the availability, wherein the order comprises the recommended laboratory test for the patient;
receiving, by the pass through server and via the web portal, a plurality of selections made on the electronic device of the health care provider to define a presentation customization, the plurality of selections including a selection for displaying raw data, a selection for displaying historical medical information, and a selection for displaying graphical indications;
dynamically generate a test result report in accordance with the presentation customization; and
electronically send the test result report to at least one of the patient or the health care provider.

* * * * *